United States Patent [19]

Meretsky et al.

[11] 4,256,116
[45] Mar. 17, 1981

[54] TRANSCUTANEOUS PAIN RELIEVER

[75] Inventors: Paul L. Meretsky; Amiram Carmon, both of Haifa, Israel

[73] Assignee: Technion Research and Development Foundation, Limited, Haifa, Israel

[21] Appl. No.: 921,344

[22] Filed: Jul. 3, 1978

[51] Int. Cl.³ .............................................. A61N 1/36
[52] U.S. Cl. .................................................... 128/421
[58] Field of Search .............. 128/419 R, 420 R, 421, 128/422, 423 R, 419 PG, 419 PS

[56] References Cited

U.S. PATENT DOCUMENTS

| 2,838,672 | 6/1958 | Paust ..................................... 128/422 |
| 3,195,540 | 7/1965 | Waller ............................. 128/419 PG |
| 3,255,753 | 6/1966 | Wing ..................................... 128/421 |
| 3,478,744 | 11/1969 | Leiter ................................. 128/423 R |
| 3,646,940 | 3/1972 | Timm et al. ........................... 128/421 |
| 3,911,930 | 10/1975 | Hagfors et al. ....................... 128/421 |
| 3,983,881 | 10/1976 | Wickham .............................. 128/421 |
| 4,084,595 | 4/1978 | Miller .................................... 128/422 |

Primary Examiner—William E. Kamm
Attorney, Agent, or Firm—Holland, Armstrong, Wilkie & Previto

[57] ABSTRACT

A transcutaneous pain reliever which utilizes a plurality of battery powered inductive energy generators, which are sequentially and individually activated, a clocking system which has means for automatically inhibiting pulsing of an energy generator until a previous energy generator has delivered its energy, and an antiadapt system to prevent a patient from becoming acclimated to the sensations. The invention also includes an energy absorption sensor which will indicate the amount of energy not absorbed by the electrodes, a bridged, transformerless battery charger which will permit the use of inexpensive low power diodes and a battery saver which may be used to permit excess energy to charge batteries.

123 Claims, 8 Drawing Figures

TRANSCUTANEOUS PAIN RELIEVER

The present invention consists of a transcutaneous pain reliever which relieves pain by the electrical stimulation of part of a patient's body.

While the mechanics of suppressing pain by electrical impulses is not yet completely known, two theories appear to have been developed. In one theory, the electrical impulses arrive at the central nervous system faster than the pain impulses in order to modulate the pain impulses. This theory indicates that electrical impulses travel through the larger nerve fibers at greater speeds whereas pain impulses travel through the smaller nerve fibers at slower rates.

A more recent theory which has been developed is the so-called "gate control" theory. According to that theory, pain relief is achieved because of the inhibition of certain nerve fibers by electrically activating the larger nerve fibers. There is a "gate" in the spinal cord which blocks pain signals from reaching the brain. This gate is closed by electrical stimulation of the larger nerve fibers so as to block pain signals to the brain coming through the smaller nerve fibers.

Regardless of the accuracy of either theory, various instruments using electric impulses to inhibit or suppress pain have been commercially available for many years. These existing instruments operate by exciting only a few electrodes attached to certain affected areas of the patient's body and are believed to be inadequate because of the limited areas stimulated. If larger numbers of electrodes can be used, then larger areas can be stimulated to produce more effective pain relief. However, increased stimulation area cannot be achieved by simply increasing electrode size since most of the energy flows between the closest points of approach of the electrodes. In addition, increasing excitation between electrodes will increase the current density through the skin. Furthermore, electrodes may inadvertently touch each other or be fired simultaneously or be superimposed on each other. These conditions may result in a sensation which may be more painful than the pain to be alleviated.

Hence, current instruments do not lend themselves to simple modification to accomplish the main objects of this invention, i.e. increasing the stimulation area without danger of injury to the patient and provide a form of stimulation which permits rather than forces the tissue to accept energy. Some of them deliver pulses of adjustable constant current at variable repetition rates. Others have adjustable compliance and some are capable of supplying the electrodes either simultaneously or alternately. Still others supply unipolar excitation while some supply bipolar ones. Not all of the current instruments are constant current types. Some are high impedance pulse generators, others modulate the peaks of the pulses while others do not. There appears to be as many waveforms as there are manufacturers with no consensus as to what is the best.

The present invention provides an improved transcutaneous pain reliever which solves the above problems and uses multiple electrode pairs which will permit an increase in the area of stimulation without increasing current density so that there is no danger or unpleasant sensation to the patient.

Another object of the present invention is the provision of an improved transcutaneous pain reliever in which electrode pairs are excited sequentially so that there is no increase of excitation to the injurious level, such as might occur if electrodes were excited together, which is important since during use there is no guarantee that electrodes will not touch each other or may not be superimposed on each other.

Another object of the present invention is the provision of an improved transcutaneous pain reliever in which the circuitry is such that there is no danger of the various electrodes firing together.

Another object of the present invention is the provision of an improved transcutaneous pain reliever which is unable to cause injury in any conceivable failure mode.

Another object of the present invention is the provision of an improved transcutaneous pain reliever in which the energy generators use inductively stored energy.

Another object of the present invention is the provision of an improved transcutaneous pain reliever in which an electrode energy absorption sensor is provided in order to determine actual energy not absorbed by the electrodes.

Another object of the present invention is the provision of an improved transcutaneous pain reliever which uses an improved clocking system for energizing the various electrodes individually with the clocking system devised so that more than one generator cannot operate at the same time.

Another object of the present invention is the provision of an improved transcutaneous pain reliever which incorporates therein an "antiadapt" system in order to prevent the patient from becoming acclimated to the electrical impulses.

Another object of the present invention is the provision of an improved transcutaneous pain reliever in which a transformerless, bridged battery charger is used to permit inexpensive low power low voltage signal diodes to be used independent of the magnitude of a much higher charging voltage source.

Another object of the present invention is the provision of an improved transcutaneous pain reliever in which the battery charger is automatically mechanically disconnected from the main patient connectable circuitry when it is charging.

Another object of the present invention is the provision of an improved transcutaneous pain reliever in which a battery saver is provided so that excess energy not delivered to electrodes can be returned to the batteries.

Other and further objects of the invention will be obvious upon an understanding of the illustrative embodiment about to be described, or will be indicated in the appended claims, and various advantages not referred to herein will occur to one skilled in the art upon employment of the invention in practice.

A preferred embodiment of the invention has been chosen for purposes of illustration and description and is shown in the accompanying drawings forming a part of the specification, wherein.

Figure 1:
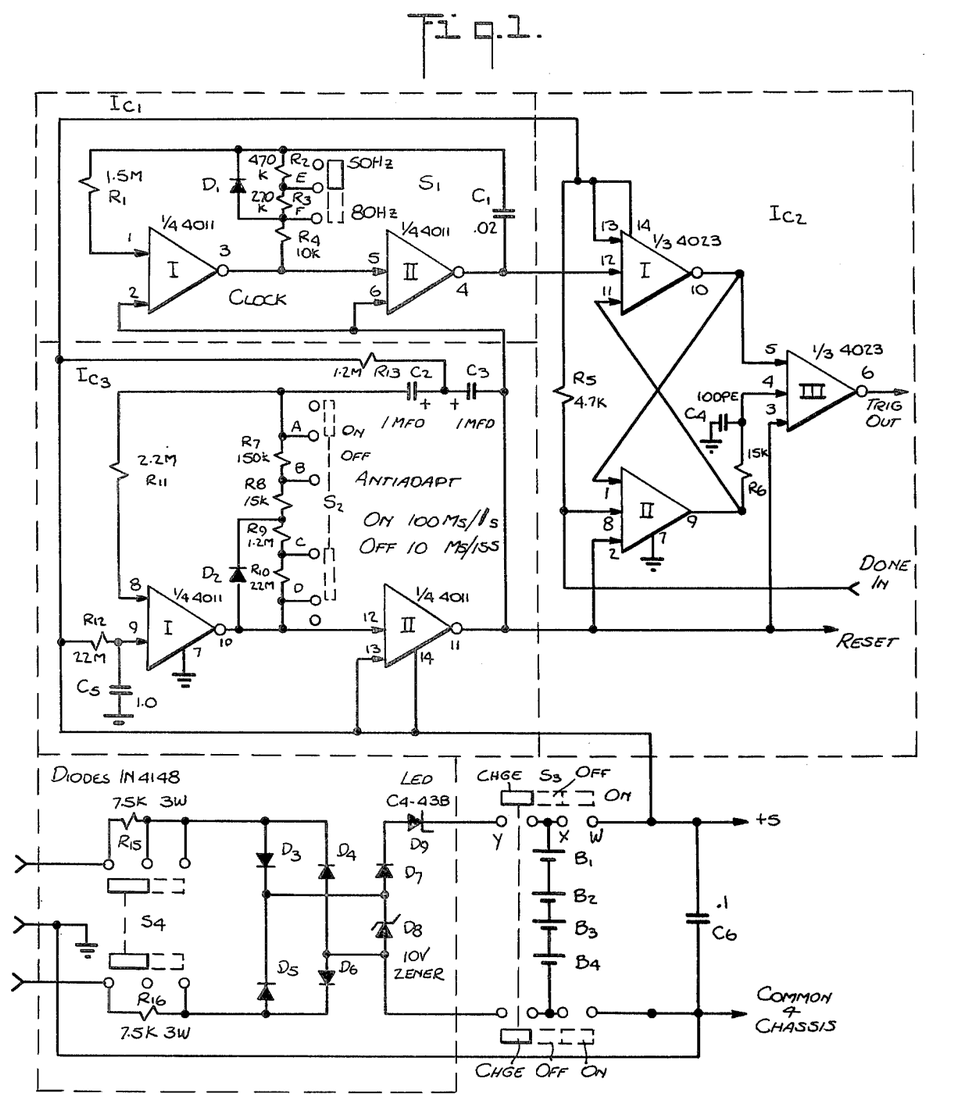
FIG. 1 is a schematic view showing the circuitry of the battery charger, the clocking system and the antiadapt system used in accordance with the present invention.

The battery charger of the present invention is shown schematically in FIG. 1. The power for the instrument is obtained from a plurality or chain of batteries B1 to B4. A switch S3 controls the battery chain connections between CHARGE, OFF and ON.

The charger unit is a bridged, transformerless bridge rectifier unit which permits the use of low voltage inexpensive diodes (such as 25 V PIV,) on a 230 volt line. The battery charger comprises diodes D3, D4, D5 and D6 which are arranged as a bridge. A zener diode D8 is used across the output of the bridge. Zener diode D8 permits the batteries B1 and B4 to be disconnected from the bridge without subjecting the bridge diodes to large inverse voltages. The voltage passing zener D8 is no larger than the breakdown voltage of zener D8 so that the zener diode D8 protects the low voltage bridge diodes D3 to D6 when the battery is disconnected from the charger and the charging circuit is still receiving power from the main power line.

Since the voltage of zener D8 is greater than the battery voltage, the zener D8 has no effect when the batteries B1-B4 are connected to the charger by switch S3. However, if the batteries B1-B4 are disconnected from the charger, the zener D8 absorbs the charging current while insuring that the maximum voltage across the bridge diodes D3-D6 is only slightly greater than it would have been with the batteries in place. Thus, even though the charging voltage supply is very high, the bridge diodes D3-D6 require a rating only slightly greater than that of the zener diode voltage of D8 which in turn is only slightly greater than the battery voltage.

The voltage of the zener diode D8 depends upon the battery requirements and, in the example illustrated, is preferably between 10 and 15 volts. The batteries B1-B4 are 150 milliamperehour batteries which may be recharged at 15 milliamperes. Preferably, they are nickel cadmium batteries of about 1.41 volts approximately, so that the battery chain total is 5.64 volts. The LED D9 requires about 1.6 volts and the reverse voltage protection diode D7 requires about 0.7 volts. Hence, breakdown voltage of zener diode D8 is such that no current passes through it when the battery assembly B1-B4 is connected to the bridge D3-D6 by switch S3 being in the CHARGE position. Under such circumstances, the voltage from D7 to the cathode of zener D8 is approximately 8 volts so that if D8 is of greater voltage, e.g. about 10 volts, no current passes.

When the switch S3 is not in the CHARGE position but in the OFF or the ON positions, the output of the bridge D3-D6 is absorbed by zener diode D8. The current is limited by the resistors R15 and R16 to about 15 milliamperes under either 230 volt or the 115 volt depending upon the position of switch S4, some contacts of which are not used as a switch but rather as a set of points on which to mount the resistor R16. The inclusion of zener D8 across the bridge D3-D6 with the accompanying voltage dropping resistors prevents the diodes in bridge D3-D6 from being subjected to any voltage greater than the breakdown voltage of the zener diode D8 in all positions of battery switch S3.

The energy generator chassis circuitry is incorporated in a circuit separate from the control chassis containing the batteries so that the physical interconnection of the two circuits makes it impossible to recharge the batteries while they are connected to the energy chassis. Hence, there can be no physical connection between the main power line and the person undergoing treatment while the batteries are being charged since the batteries must be separated from the control chassis before they are charged.

The improved clocking system of the present invention is designed to operate the numerous electrodes individually and sequentially. Experimentally, it has been verified that about 30 to 40 excitations/second no perceptual changes are felt at threshold level, whereas above threshold levels, a few subjects perceive the difference between 40 and 80 Hz and none over 80 Hz. At the low battery voltage it can take as long as 2 milliseconds to store the maximum energy. The clocking system must insure against more than one generator operating together and, in accordance with the present invention, the clock is automatically inhibited until the last generator in the chain of generators has delivered its energy.

In addition, it has also been found that as time passes, there is a decreasing sensory perception, or acclimitization, at constant energy. An "anti-adapt" system has been devised to avoid this. While it is not necessary to "feel" the stimulations for effectiveness, there is a tendency for the therapist, as well as the patient, to require some sort of a sensory effect. Based on the fact that step changes in energy of a few percent can be felt, a system of clock modulation was devised which stops excitation approximately 10% of the time of a ½ to 2 second base when the "Anti-adapt" is "on" and about 10$\phi$ ms of a 20 second base when it is "off".

This "anti-adapt" system is also useful to determine defective energy generators since the chain stops in the absence of a trigger pulse to the next generator so that the last generator never signals the clock to operate the first generator and the energy absorption sensor (described more fully hereinafter) indicates that the stage has failed.

The upper portion of FIG. 1 shows the Clocking System and the Anti-adapt System. The central chassis circuitry consists of two multi-vibrators $IC_1$ and $IC_3$ (comprising IC4011) and is a standard and well known CMOS quad NAND gate which is available from a number of manufacturers. In general, the clocking system consists of a multi-vibrator $IC_1$ made up of gates I and II with pins 1, 2 and 3 and 4, 5 and 6, respectively.

This multi-vibrator may be a well known RCA multi-vibrator in which a diode D1 is used to create as asymmetric clock. Based on the position of switch S1, the output repetition rate is 50 or 80 Hz at pin 4. If desired, S1 may be replaced by a potentiometer and a fixed resistor to permit the clock to be variable rather than preset.

It is also possible to substitute for the 2 leg NAND gate of the clock $IC_1$, the equivalent function of a 2 leg NAND Schmitt trigger, which is also of CMOS construction. The internal regenerative action of the Schmitt trigger reduces battery drain because of reduction in the time during which the series transistors in the output of the gates can conduct from the power supply to common. This would reduce the load on the batteries.

Pins 2 and 6 of multi-vibrator $IC_1$ connect together to the output of an antiadapt multi-vibrator $IC_3$ having gates I and II with pins 7 to 10 and 11 to 14, respectively. The antiadapt multi-vibrator $IC_3$ has a switch S2 which modulates the clock. If S2 is in the "on" position, the main clock output of pin 4 is inhibited for approximately 100 milliseconds out of every second. If S2 is in the "off" position, the multi-vibrator $IC_1$ operates more slowly and is considerably more asymmetric, i.e. the output of pin 4 is inhibited about 10 milliseconds out of approximately every 10–20 seconds. The frequency is controlled by capacitors C2 and C3, which are identical, with the effective capacitance being halved by the series connection. If electrolytic capacitors are used at C2 and C3, resistor R13 is provided to prevent reverse bias. If monolytic capacitors are to be used, the capacitor C2 may be replaced by a short circuit and resistor R13 is eliminated so that only C3 remains.

Pins 13 and 9 are interconnected so that when the instrument is turned on, and receives power from the batteries B1–B4, pin 13 rises with the power switch output at 3, but pin 9 is delayed. Pin 9 is allowed to rise with a time constant which is a product of resistor R12 and capacitor C5. With pin 9 remaining at ground potential longer than pin 13, the output 10 of gate I is held at a "1" and with pin 13 of gate II also at "1", the multi-vibrator is inhibited. The output on pin 11 is held at "0" until pin 9 rises to "1" at which time the multi-vibrator $IC_3$ is released. Pin 11 is a RESET to all the energy generators. Hence, the energy generators are conditioned to be in the "off" position when the instrument is turned on. American Association for Medical Instrumentation Regulations suggest a long turn-on delay for instruments without switches on outputs. The time constant R12 C5 generates approximately a 15 second delay to conform to the requirements.

The clock output pin 4 of $IC_1$ enters a trigger circuit $IC_2$ which is a separate CMOS integrated circuit and which may be a triple NAND gate type 4023. This trigger circuit comprises a flip-flop with pins 10, 11, 12 and 13 on gate I and pins 1, 2, 8 and 9 on gate II. The clock output at 4 comes in while pin 10 of gate I is in the "1" condition, at which time pin 9 of gate II, which has been in the "1" condition, goes to "0". R6 and C4 is a delay circuit which permits a brief pulse of about 15 microseconds to issue from pin 6 of gate III. The output on pin 10 remains at a "1" and pin 9 remains at "0" until either a DONE IN signal arrives at pin 8 of gate II or a RESET occurs on pins 2 of gate II and 3 of gate III. At that time, the clock output 4 operates on pin 12 of gate I. The RESET causes pin 4 to be in the "1" condition while pin 11 is in the "0" condition so that no TRIG OUT occurs during RESET of the energy generator.

Figures 2, 3:
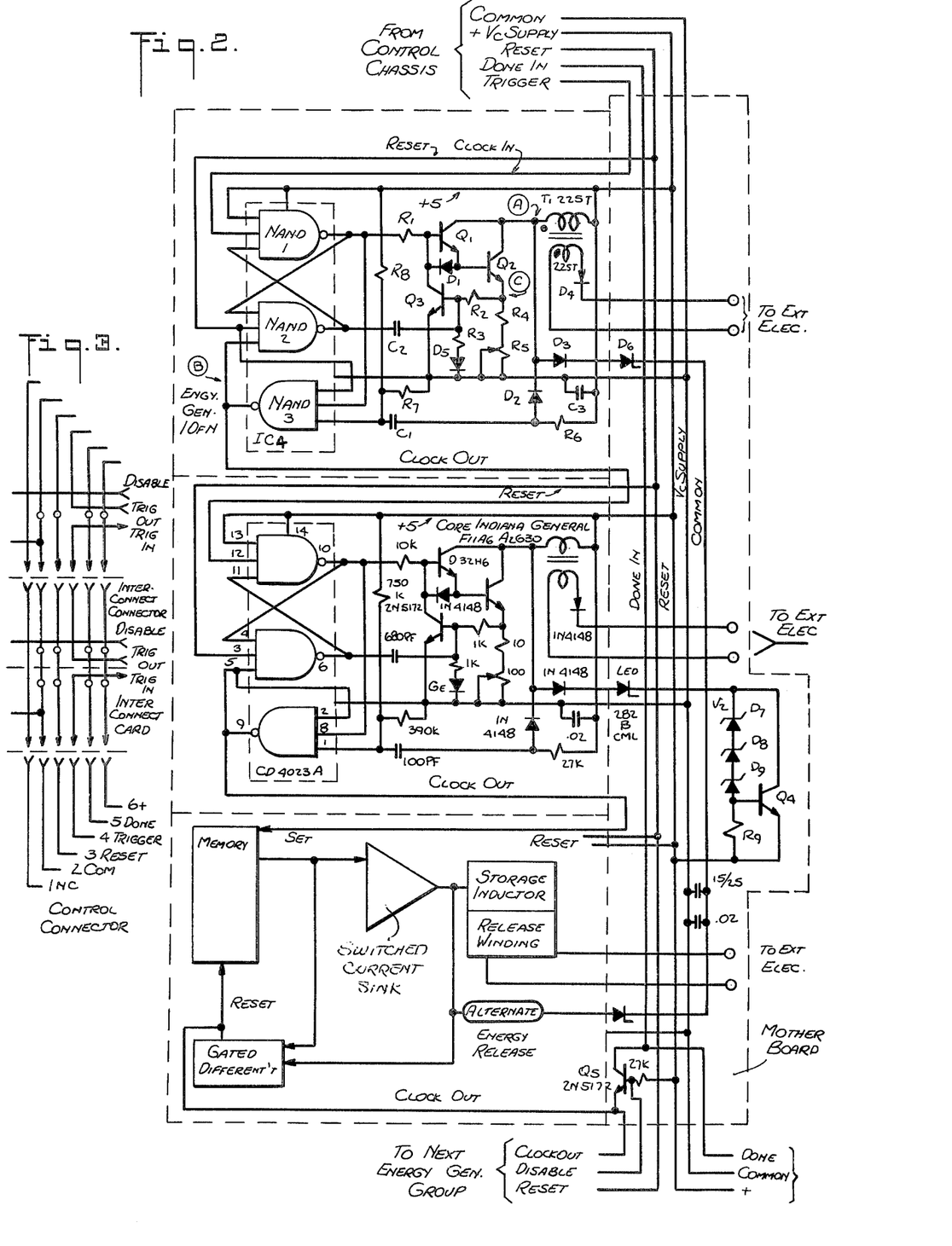
FIG. 2 is a schematic view showing an energy generator of the present invention with the lower part showing the parts in block diagram form, the central part showing the recommended values for the parts and the upper part showing the parts used.
FIG. 3 is a schematic diagram showing the circuitry between the control connectors and the energy generators.

Referring to FIG. 2, the DONE IN signal is a completion signal from the last connected energy generator. Each energy generator chassis consists of a number of generators. In the present application, six generators are used so that there are six identical boards interconnected to a mother board which has a control transistor Q5 (2N5172). The connector which permits the control chassis to power the energy generator chassis has five active pins in the interconnecting connector while the connector which permits subsequent energy generators to be connected consist of six pins (see additional DISABLE pin).

As shown in FIG. 3, if an additional energy generator chassis is plugged into the first energy generator chassis, the control transistor Q5 is inhibited (see DISABLE on its base) from operating because no output exists on the common DONE IN line. It is only the last stage of the last chassis which drives the control transistor Q5 so that while there are as many Q5 transistors as there are generator chassis, only the last one will be permitted to operate.

If the DONE IN signal does not arrive between successive clock pulses, no TRIG OUT signal from pin 6 (FIG. 1) will arise until a DONE IN occurs so that the clock rate is, in effect, divided by two, if the time required to operate all the energy generators results in a DONE IN signal arriving after the second clock pulse and before the third. It is also possible to release the clock immediately upon receipt of a DONE IN signal if a clock pulse has been missed.

In connection with the energy generator of the present invention, the energy is stored inductively. An inductance $T_1$ (FIG. 2) is used in each of the energy generators, the secondary winding of which is connected to the electrodes.

In general, energy may be stored either inductively or capacitatively. Capacitive storage of energy is not desirable in a system whose outputs must be isolated from each other because the energy must be delivered through a transformer or some other isolator. In addition, capacitor voltages are high and transformer failure may result in dangerous situations.

However, inductor storage of energy is possible from a relatively low supply voltage. The energy stored is $\frac{1}{2} LI^2$, if L is in henries and I is in amperes, the energy is in watt-seconds. The time T required to attain a given current is $T = LI/V$ where the resistance of the inductor is negligible, V is the effective supply voltage, I is the current, L is the inductance and T is in seconds.

It has been experimentally determined that energies between $10^{-6}$ and $2 \times 10^{-4}$ watt-seconds, which, respectively, correspond to subsensory and painful forced muscle contraction, were desirable. The energy is created by storage on a $25 \pm 5$ millihenry inductor $T_1$ which is formed by winding 225 turns of #34 wire on $\frac{1}{2}$ of the bobbin of an 18 mm Dia ferrite pot core having an $A_L$ of 630. This particular ferrite core is able to store the maximum energy only just prior to saturation so that there is no possibility that the inductor can deliver such more than the maximum energy desired.

Operating room conditions demand the use of no more than about 6 volts without danger. In order to avoid the problem of possible transformer breakdown and because of portability considerations, the present invention uses a battery operated instrument. Batteries change their voltage as a function of residual capacity, so that a series connection of four fully charged Ni-Cd batteries initially deliver about 5.64 volts (5–10% capacity used), about 5 volts most of the time (80% capacity) and rapidly discharge to 0 in the last 10% of capacity. In order to achieve the maximum interval between battery recharge it is necessary to regulate the energy since a change from 5.64 to for example, 3.5 volts would lead to a decreased storage energy of 37.8% as the battery output decayed. The energy may be regulated by controlling either the effective battery voltage, controlling the time of connection of the inductor to the battery or controlling the current in the inductor. The control must be effective over the entire energy range and for the inductor $T_1$ is from approximately 5 to 100 milliamperes. The inductor should have no energy stored except prior to release so that the energy must be switched in such a way that only one of a series of generators, each of which provide their isolated output to a pair of electrodes, can be activated at one time.

Because of the large number of generators contemplated, each with the two electrodes, the invention includes a method of determining the amount of energy not absorbed by the electrodes.

The energy generators and absorption sensor of the present invention is shown in FIG. 2. The energy generator IC4 comprises gates NAND 1 and NAND 2 which make up a flip-flop with NAND 1 initially having its output in the "0" condition and NAND 2 having its output in the "1" condition. Thus, transistors Q1 and Q2 are held in the "off" condition since no base current is available for Q1. Q1 and Q2 are preferably a Darlington pair modified by D1 which bridges the emitter-base of Q1 and is used to accelerate shut-off of Q2. When a clock pulse arrives, the output of NAND 1 raises and Q1 and Q2 saturate since the collectors cannot obtain sufficient current from the inductor.

Figure 6:
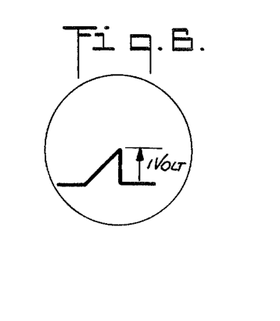
FIG. 6 shows the waveform generated at point C of FIG. 2.

The voltage on the collector side of the inductor falls almost to common and remains in this condition until point C, the waveform of which is shown in FIG. 6, or the voltage caused by the current through R4, R5, is sufficient to turn on Q3. When Q3 turns on, its collector stabilizes the base voltage of Q1 so that the current in the inductor T1 can no longer increase. At this point, the collector voltage of Q3 rises abruptly to the supply voltage, which may be approximately +5. This increase in voltage is now communicated to NAND 3 through C1 by current through R6 because the junction of C1R6 is no longer clamped by D2.

R7, R8 and C1 make up a differentiator with R7 and R8 used to establish a DC bias level for the differentiator and its time constant. If the number of stages of energy generation is large or there is no mother board, it is possible to save one resistor per energy generator at the cost of 2 resistors which are used to set a common bias level. To establish the differentiator reference level, the present design uses 2 N resistors, it is possible to use N+2 resistors where N is the number of energy generators.

Figure 4:
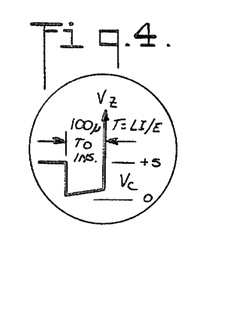
FIG. 4 shows the waveform generated at point A of FIG. 2.
Figure 5:
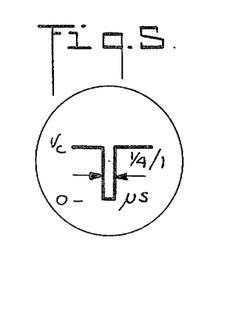
FIG. 5 shows the waveform generated at point B of FIG. 2.

The input leg of NAND 3 to C1 is normally biased ⅓ of the supply voltage above ground. When the voltage at point A (the waveform of which is shown in FIG. 4) rises abruptly, because the other two legs of the gate NAND 3 are in the "1" condition the output of NAND 3 falls to "0". This resets gate NAND 2 which in turn alters the state of NAND 1 via the connection between pins 6 and 11 and at the same time generates an output which is preferably the narrowest output pulse possible consistent with the given gate chain. NAND 3 not only resets the memory assembly of its own generator but also sets the memory assembly of the next generator. In the last generator, however, NAND 3 causes Q5 to activate a DONE IN signal, as well as reset its own memory.

The connection between the output of NAND 1 and one of the input legs of NAND 3 gaurantees an output pulse width of two propagation delay times, only one of which is required for the next energy generator. Thus the output from NAND 3 is a fairly narrow pulse (approximately 400 NS) guaranteed to be wide enough to operate the next stage and at the same time narrow enough to prevent a signal other than the valid one from being pulsed from the output of NAND 3. This is important since subsequent electrodes, or subsequent energy generators can, if the electrodes from a previous generator are geometrically disposed, permit current to pass through the output winding of a previous stage. If the differentiator were not gated then a false trigger signal could be supplied. Because of the interconnection of NAND 1 and NAND 3 there is no possible method of generating a false trigger signal.

When NAND 1 and NAND 2 are altered by NAND 3 the output of NAND 2 forces Q3 into heavy conduction by reason of the capacitor C2. This quickly shuts off Q1 directly and Q2 via D1. The shut-off is rapid enough so the energy that was stored in the inductor $T_1$ cannot dissipate through Q1, Q2. It must dissipate either through D3 and D6, in which case LED D6 will illuminate, or through the secondary winding of $T_1$ through D4 to the external electrodes.

If the external electrodes are properly connected, then the voltage at A will not rise enough to pass current through D6 since the voltage required is the voltage necessary to pass current through D7, D8 and D9 on the mother board. D7, D8 and D9, Q4 and R9 form a power zener diode, or a low impedance zener diode. The diodes, are normally 33 volt zeners, having an accumulated sum of about 100 volts. If the voltage on the collector of Q1, Q2 exceeds 100 volts current passes through D6 and the LED lights up. If the energy does not pass through D6 then it must have passed out the secondary winding of $T_1$.

If for any reason Q3 fails in the open condition the circuit will continue to operate. The current rises in the inductor and when it reaches core saturation the inductance falls very rapidly and voltage can no longer be supported across the core winding since the inductance falls to "0" or very close to "0". Under this situation a pulse is still delivered to the gated differentiator and a subsequent trigger to the succeding stage, however, since the inductor $T_1$ has been chosen to saturate at slightly more than the maximum energy, an unsafe condition does not exist. Under every other situation of failure, i.e. Q3 failing as a short, the generator fails to do anything and no trigger pulse is generated from the gated differentiator and the firing for the remainder of the chain is halted until a RESET occurs. The energy generators will fire sequentially during failure up to the failed stage and no further, therefore it is possible with the electrodes disconnected to examine the light pattern from D6 LEDs and determine the last stage to operate. The stage following that is defective.

Capacitor C2 speeds up the shut-off of Q1, Q2 which is important at the lower currents. At the maximum value of R5, very little energy is placed on the primary of $T_1$ and if $Q_1$, $Q_2$ do not shut off rapidly then the energy stored in the inductor $T_1$ will be lost to Q1, Q2 during shut-off.

Another function of C2 is to stabilize the current regulating loop. The output of NAND 2 is near either common or the positive supply by reason of the nature of the CMOS integrated circuit, the effective series resistance of about 500 ohms is considered almost negligible. The current regulator ($Q_1$, $Q_2$, $Q_3$ and associated parts) is effective, restricting changes in output energy to approximately 5% for a supply voltage swing of 3½ to 10 or 12 volts. The diode D5 is a germanium or Shottky diode whose purpose is to temperature compensate the regulator loop, including the ferrite core of $T_1$, D4 restricts the direction of energy delivery and this restriction is associated with the absence of any unpleasant sensations under the electrodes.

The regulator arrangement permits delivery of constant watt-seconds per pulse to pairs of electrodes, independent of the state of the battery supply (as long as there is sufficient voltage for the circuit to operate at all). The energy is stored in the ferrite core $T_1$ by controlling the flux density in the core which is done by the primary winding connected to the feed back current regulator which will turn itself off when the current commanded by the adjustable potentiometer (R5) has been reached. The energy ($\frac{1}{2} LI^2$) is inhibited from leaving via the current regulator loop because it ceases to be able to conduct after it is satisfied. The energy in the core $T_1$ is free to leave by one of two alternative paths, i.e. through a secondary winding to the tissue-electrode system or via the primary alternate absorption system of D3, D6, D7, D8, D9, R9 and Q4. The secondary winding is isolated from the tissue during energy storage by a series diode D4. The voltage across electrodes in good contact with the skin does not exceed 30 to 40 volts maximum when 100 milliamperes flows. If the voltage across the electrodes does not exceed acceptable values, e.g. approximately 90 volts, all the energy is sent to the tissue-electrode system. If it is in excess of 90 volts, the electrode contact is not good and the energy is released to both the electrode tissue system and through LED D6. That portion of the energy which passes through the LED D6 illuminates it, thereby alerting the therapist that the electrodes associated with that particular energy generator are in poor contact. The brighter the LED the poorer the electrode contact with no connection causing the brightest conditions.

The present invention also envisions the use of a battery saver if large numbers of energy generators are connected but only a few are used. Energy stored on the inductor but not delivered to the electrodes can be returned to the battery. A third winding would be incorporated on the core bobbin and the LED absorption sensor system moved to the additional winding. In order to be effective an energy spreader, consisting of a capacitor and a transistor as well as resistors, is used to meter the returned energy slowly in comparison to its availability since the battery electrochemical characteristics will not permit recharge by extremely short pulses.

Figure 7:
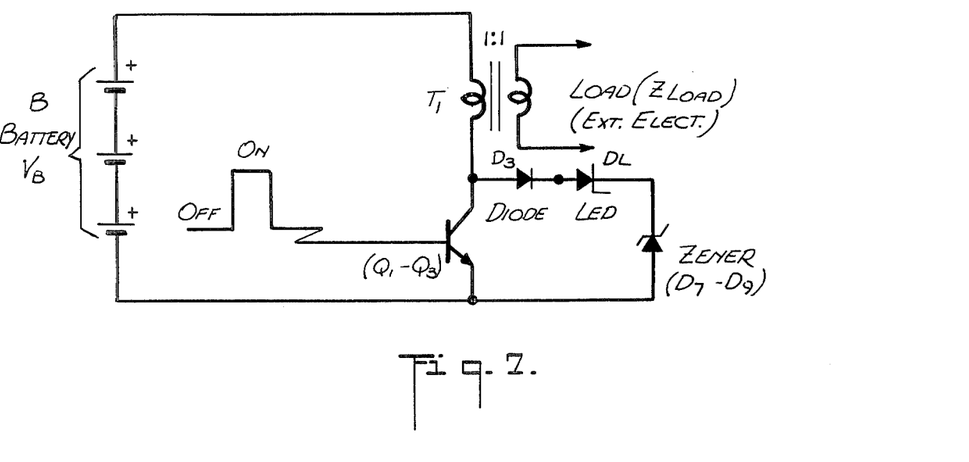
FIG. 7 is a diagramatic view of a simplified version of the energy generator as shown in FIG. 2.
Figure 8:
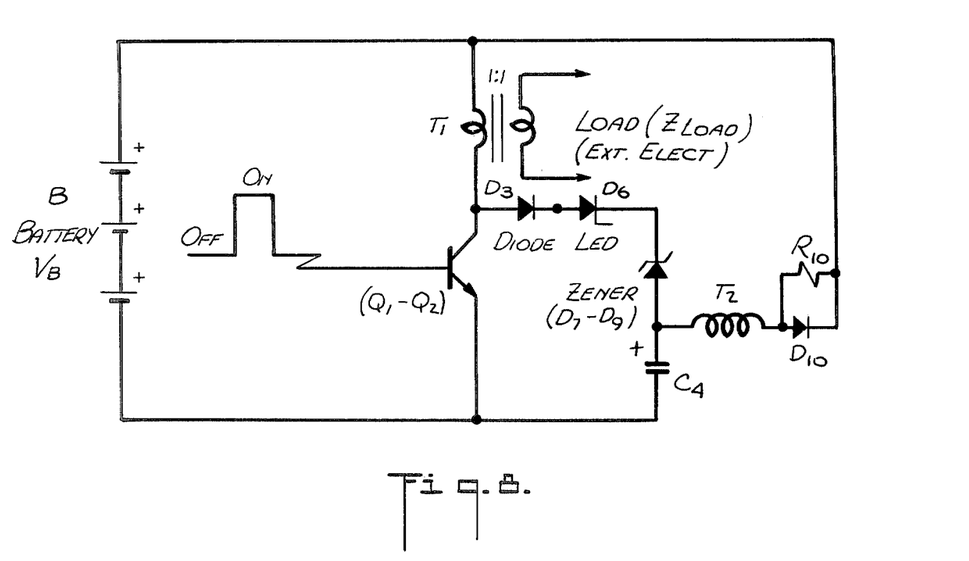
FIG. 8 is a view similar to FIG. 7 showing the use of a battery saver energy spreader circuit.

This battery saver feature with an energy spreader is illustrated in FIGS. 7 and 8.

FIG. 7 is a diagrammatic simplified version of the energy generator shown in FIG. 2 which has been described above and which has an indicator circuit which illuminates an LED D6 if the energy available from the inductor $T_1$ is not absorbed by the load at a voltage lower than the zener breakdown voltage of zener diodes D7-D9. The effective zener breakdown voltage consists of Vz+Vled+Vdiode, where Vled+Vdiode are the foreward voltage drops across these elements.

When transistors Q1 and Q2 are turned off, the energy in $T_1$ is $\frac{1}{2}LI^2$, where I is the current in the inductor at the time the transistors are turned off. At this time, the energy is dissipated in either the external electrodes or in the indicator circuitry or the transistor circuit. Vz effective must be chosen so that the transistor breakdown is not an available energy sink. For that interval that IZload>OR=Vz effective, the energy is discharged into both the external electrodes and the indicator circuitry. When there is no external load, all the energy is absorbed by the indicator circuitry and would ordinarily be wasted. However, the energy not absorbed by the external load may be conserved, i.e. returned to a rechargeable battery B provided that the form in which the energy is returned is compatible to its acceptance by the electrochemical system that makes up the battery B.

To be compatible the recharge voltage must be greater than that of the battery and the charge must be distributed in time for an interval which is long compared with the time required to satisfy the electrochemical requirements associated with recharge. In the present structure, the duration for direct energy recovery from the condition occuring with an open circuit-no load situation at the output is too short. The electrochemical system will not, for instance, recognize submicrosecond and microsecond energy pulses as being suitable for charge recovery. In order to make the energy recoverable it must be stored and fed back to the battery more slowly.

FIG. 2 shows a circuit for spreading the energy and recharging a battery. This may be the original batteries B1-B4 used to supply power to the unit or it may be a separate battery. Instead of being returned to common, the zener diodes D7-D9 are returned to a capacitor C4 which is connected to the battery B through an inductor T2. The inductance of T2 is large enough so that essentially no current flows through it for short term changes on C4. The voltage on C4 is essentially Vb. The energy that was in $T_1$ will, if it does not exit through the external load, find its way onto C4 (neglecting resistive losses associated with Va, Vd, & Vled). This will result in a voltage increase ($\Delta V$) on C4 such that $\Delta V = I(L/C)^{\frac{1}{2}}$. The incremental voltage will lead to a current (whose driving voltage is $\Delta V - Vd$) which is slowly metered into the battery B by the impedance of the inductor T2.

The use of the resistor R10 across the diode D10 permits the energy to be placed on C4 from voltage Vb. The metering time consists of the size of C4 and T2 and depends on the interval between energy availabilities from $T_1$ as well as the restrictions of the electrochemical system. Storing the energy on C4 increases the effective peak zener voltage by $\Delta V$. Vz effective=Vz+Vd+Vled+Vb and the sum must be less than the collector to emitter breakdown voltage of the transistors Q1-Q2. A lower value of Vz may require selection of zener diodes having a lower breakdown potential.

It will thus be seen that the present invention provides an improved transcutaneous pain reliever having multiple electrode pairs to increase the area of stimulation while at the same time keeping the current density constant without any danger to the patient because of increased voltage or any conceivable failure mode. The invention also provides for an improved energy generator in which energy is stored inductively with an improved electrode energy absorption sensor to determine actual energy not absorbed by the electrodes and provides an improved clocking system in which the various electrodes are not fired together but sequentially activated. The invention further provides an "antiadapt" system in order to prevent the patient from becoming acclimated to the sensations and includes the use of an improved battery saver so that energy not delivered can be returned to the batteries. The battery charger used with the present invention is transformerless and is zener bridged to permit the use of signal diodes for charging purposes and which is automatically disconnected when being charged.

As many and varied modifications of the subject matter of this invention will become apparent to those skilled in the art from the detailed description given hereinabove, it will be understood that the present invention is limited only as provided in the claims appended hereto.

The embodiments of the invention in which an exclusive property or privilege is claimed are defined as follows:

1. A transcutaneous pain reliever comprising a plurality of external electrode assemblies for supplying electric excitations to a patient, means for sequentially and individually pulsing current through said external electrode assemblies, means to prevent pulsing of current through one external electrode assembly, means responsive to the completion of a pulse from a previous external electrode assembly to pulse current through said one external electrode assembly, said external electrode assembly comprising means for inductively storing energy and means for releasing said energy to the external electrodes, said inductive storage means comprising a storage winding for storing the energy and a release winding for releasing said energy to the external electrodes.

2. A transcutaneous pain reliever as claimed in claim 1, wherein an energy absorption assembly is provided to receive the signal if the voltage on the primary is larger than a predetermined amount.

3. A transcutaneous pain reliever as claimed in claim 2, wherein said energy absorption assembly comprises a zener diode assembly in circuit with the primary winding.

4. A transcutaneous pain reliever as claimed in claim 3, wherein said absorption sensing assembly comprises an LED in circuit with the zener diode assembly.

5. A transcutaneous pain reliever as claimed in claim 4, wherein said zener diode assembly comprises at least one zener diode, a resistance and a transistor.

6. A transcutaneous pain reliever as claimed in claim 5, wherein a diode is interposed between said primary and second LED.

7. A transcutaneous pain reliever as claimed in claim 6, wherein any energy exceeding accepted voltage values will pass through the LED to illuminate it.

8. A transcutaneous pain reliever comprising a plurality of external electrode assemblies for supplying electric excitations to a patient, means for sequentially and individually pulsing current through said external electrode assemblies, means to prevent pulsing of current through one external electrode assembly, means responsive to the completion of a pulse from a previous external electrode assembly to pulse current through said one external electrode assembly a clocking assembly is provided, said clocking assembly being connected to means for operating the external electrodes, a multi-vibrator, the output of the mutivibrator supplying a pulse to a trigger circuit, said trigger circuit being connected to means for operating the external electrodes.

9. A transcutaneous pain reliever as claimed in claim 8, wherein said multi-vibrator includes a pair of gates, said gates being connected to said trigger circuit and adapted to supply pulses to said trigger circuit.

10. A transcutaneous pain reliever as claimed in claim 9 wherein a diode is provided with said multivibrator, and a pair of resistor means in circuit with the diode to create an asymmetric clock.

11. A transcutaneous pain reliever as claimed in claim 10 wherein a switch is provided in the multi-vibrator, said switch being movable into circuit with either of said resistor means to vary the repetition rate of the output.

12. A transcutaneous pain reliever as claimed in claim 10 wherein a potentiometer and a fixed resistor is in circuit with the diode to permit the clock to be variable.

13. A transcutaneous pain reliever as claimed in claim 8, wherein the said multi-vibrator includes a gate and Schmitt trigger connected to said trigger circuit and adapted to supply pulses to said trigger circuit.

14. A transcutaneous pain reliever comprising a plurality of external electrode assemblies for supplying electric excitation to a patient, means for sequentially and individually pulsing current through said external electrode assemblies, means to prevent pulsing of current through one external electrode assembly, means responsive to the completion of a pulse from a previous external electrode assembly to pulse current through said one external electrode assembly, and storage means are provided for storing energy before passage to the external electrode assembly, an absorption sensing mechanism is in circuit with said storage means to indicate the amount of energy not used by the external electrodes.

15. A transcutaneous pain reliever comprising a plurality of external electrode assemblies for supplying electric excitations to a patient, means for sequentially and individually pulsing current through said external electrode assemblies, means to prevent pulsing of current through one external electrode assembly, means responsive to the completion of a pulse from a previous external electrode assembly to pulse current through said one external electrode assembly a battery charger is provided comprising a bridge assembly having a plurality of diodes arranged in a bridge, said bridge assembly having means to permit batteries to be charged to be connected thereto, a zener diode assembly across the output of the bridge assembly, means connecting the bridge assembly to a charging voltage source, said zener diode assembly breakdown voltage being greater than the battery voltage, the bridge diode assembly voltage rating being greater than the zener diode breakdown voltage, switch means being provided to connect the diode bridge assembly to batteries which are to be charged.

16. A transcutaneous pain reliever as claimed in claim 15, wherein switch means are provided to connect the batteries to said external electrode assemblies.

17. A transcutaneous pain reliever as claimed in claim 16, wherein the switch means to connect said batteries to the external electrode assemblies is the same switch means for connecting the batteries to the zener circuit, said switch means being movable from a position in circuit with said zener circuit to position in circuit with said external electrode assemblies whereby movement of the switch means into circuit with the zener circuit will automatically electrically disconnect the batteries from the external electrode assemblies, movement of the switch means into circuit with the external electrode assembly will automatically disconnect the batteries from the zener circuit.

18. A transcutaneous pain reliever as claimed in claim 17, wherein the output of the diode bridge assembly is absorbed by the zener diode when batteries are disconnected for the diode bridge assembly.

19. A transcutaneous pain reliever comprising a plurality of external electrode assemblies for supplying electric excitations to a patient, means for sequentially and individually pulsing current through said external electrode assemblies, means to prevent pulsing of current through one external electrode assembly, means responsive to the completion of a pulse from a previous external electrode assembly to pulse current through said one external electrode assembly, an anti-adapt system being provided comprising a multi-vibrator, the multi-vibrator being connected to a clock assembly and means in said multi-vibrator for inhibiting the output of the clock assembly, a switch in circuit with said multi-vibrator with associated resistors to permit the anti-adapt clock assembly output to vary.

20. A transcutaneous pain reliever as claimed in claim 19, wherein said multi-vibrator comprises a pair of gates, the output of which are connected to the gates in the clock assembly to actuate them.

21. A transcutaneous pain reliever as claimed in claim 20, wherein capacitor means are provided in circuit with the output of said gates to control the frequency.

22. A transcutaneous pain reliever as claimed in claim 20, wherein means are provided to inhibit the multi-vibrator.

23. A transcutaneous pain reliever as claimed in 22, wherein said inhibitor means comprises means for connecting a common power source, an input to the two gates one of said gate inputs being provided with means to delay a pulse from the power source from reaching said gate.

24. A transcutaneous pain reliever as claimed in claim 23, wherein said delay means comprises a capacitor and a resistor in circuit with said delayed gate.

25. A transcutaneous pain reliever as claimed in claim 24, wherein the inhibit on the multi-vibrator is released when the said delayed pulse at the input of said delayed gate rises to the condition of the input at the other gate.

26. A transcutaneous pain reliever as claimed in claim 25, wherein release of the inhibit on said multi-vibrator causes a pulse to be released to reset the external electrode assemblies.

27. A transcutaneous pain reliever as claimed in claim 26, wherein said clock assembly is in circuit with a trigger circuit, said trigger circuit connected to the external electrode assemblies and comprising a flip-flop and a TRIG OUT gate, said flip-flop being in circuit with the multi-vibrator.

28. A transcutaneous pain reliever as claimed in claim 27, wherein a delay circuit comprising a resistor and capacitor is associated with said trigger.

29. A transcutaneous pain reliever as claimed in claim 28, wherein means responsive to the completion of a pulse from the external electrode assembly will cause the clock to operate the trigger.

30. A transcutaneous pain reliever as claimed in claim 28, wherein said pulse from the multi-vibrator alters the condition of the flip-flop to a condition different from the condition of the clock assembly.

31. A transcutaneous pain reliever comprising a plurality of external electrode assemblies for supplying electric excitations to a patient, means for sequentially and individually pulsing current through said external electrode assemblies, means to prevent pulsing of current through one external electrode assembly a previous external electrode assembly to pulse current through said one external electrode assembly and a battery saver is provided comprising a storage coil, and a charge release coil, a zener diode assembly for an absorption sensor, said zener diode assembly having a capacitor which is connected to a battery to be charged, an additional inductor coil in circuit with the zener diode assembly whereby energy not used by the release coil will be supplied to the battery to charge it through the said additional inductor coil.

32. A transcutaneous pain reliever comprising a plurality of external electrode assemblies for supplying electric excitations to a patient, means for sequentially and individually pulsing current through said external electrode assemblies, means to prevent pulsing of current through one external electrode assembly, means responsive to the completion of a pulse from a previous external electrode assembly to pulse current through said one external electrode assembly, said external electrode assembly comprising means for inductively storing energy and means for releasing said energy to the external electrodes, a clocking assembly being provided, said clocking assembly being connected to means for operating the external electrodes and storage means are provided for storing energy before passage to the external electrode assembly, an absorption sensing mechanism is in circuit with said storage means to indicate the amount of energy not used by the external electrodes.

33. A transcutaneous pain reliever as claimed in claim 32, wherein a battery charger is provided comprising a bridge assembly having a plurality of diodes arranged in a bridge, said bridge assembly having means to permit batteries to be charged to be connected thereto, a zener diode assembly across the output of the bridge assembly, means connecting the bridge assembly to a charging voltage source, said zener diode assembly breakdown voltage being greater than the battery voltage, the bridge diode assembly voltage rating being greater than the zener diode breakdown voltage.

34. A transcutaneous pain reliever as claimed in claim 33, wherein an anti-adapt system is provided comprising a multi-vibrator, the multi-vibrator being connected to a clock assembly and means in said multi-vibrator for inhibiting the output of the clock assembly.

35. A transcutaneous pain reliever as claimed in claim 34, wherein a battery saver is provided comprising a storage coil, and a charge release coil, a zener diode assembly for an absorption sensor, said zener diode assembly having a capacitor which is connected to a battery to be charged, an additional inductor coil in circuit with the zener diode assembly whereby energy not used by the release coil will be supplied to the battery to charge it through the said additional inductor coil.

36. A transcutaneous pain reliever as claimed in claim 35, wherein said pulse preventing means comprises a control transistor.

37. A transcutaneous pain reliever as claimed in claim 36, wherein said control transistor is provided for each external electrode assembly and wherein the control transistors of all but the last of said external electrode assembly being inhibited from operating.

38. A transcutaneous pain reliever as claimed in claim 37, wherein said control transistor is inhibited because no output exists on a DONE IN line common to said plurality of control transistors.

39. A transcutaneous pain reliever as claimed in claim 38, wherein a trigger assembly is provided to pulse a signal through the external electrode assemblies.

40. A transcutaneous pain reliever as claimed in claim 39, wherein said trigger assembly is inoperative until a DONE IN signal from the control transistor is received by the trigger assembly.

41. A transcutaneous pain reliever as claimed in claim 40, wherein an energy generator assembly is interposed in circuit between said external electrode assembly and the trigger assembly and wherein said energy generator assembly activates said control transistor.

42. A transcutaneous pain reliever as claimed in claim 41, wherein a memory assembly is provided in said energy generator assembly.

43. A transcutaneous pain reliever as claimed in claim 42, wherein the energy generator assembly includes a gated differentiator.

44. A transcutaneous pain reliever as claimed in claim 43, wherein said gated differentiator supplies a pulse to said memory assembly.

45. A transcutaneous pain reliever as claimed in claim 44, wherein said energy generator assembly includes a current regulator assembly.

46. A transcutaneous pain reliever as claimed in claim 45, wherein said memory assembly comprises a flip-flop assembly including a pair of gates.

47. A transcutaneous pain reliever as claimed in claim 46, wherein the current regulator circuit is in circuit with the flip-flop assembly to control the release of energy from said inductive storage means.

48. A transcutaneous pain reliever as claimed in claim 47, wherein the condition of the output of a first gate of the flip-flop assembly is changed by a pulse from the trigger assembly.

49. A transcutaneous pain reliever as claimed in claim 48, wherein said current regulator circuit includes a darlington pain and a feedback transistor.

50. A transcutaneous pain reliever as claimed in claim 49, wherein said darlington pair having its collector load connected to the inductive storage means.

51. A transcutaneous pain reliever as claimed in claim 50, wherein said darlington pair is in circuit with the said first gate of the flip-flop.

52. A transcutaneous pain reliever as claimed in claim 51, wherein the inductor load at the collector of the darlington pair causes the feedback transistor to turn on to satisfy the current regulator.

53. A transcutaneous pain reliever as claimed in claim 52, wherein voltage on the inductor increases when said current regulator satisfies to cause an increase in voltage in a leg of said gated differentiator.

54. A transcutaneous pain reliever as claimed in claim 53, wherein said increase in voltage of said gated differentiator occurs through a capacitor and a resistor.

55. A transcutaneous pain reliever as claimed in claim 54, wherein the output of said gated differentiator resets the flip-flop of said memory circuit.

56. A transcutaneous pain reliever as claimed in claim 55, wherein resetting of said memory circuit shuts off said current regulator circuit.

57. A transcutaneous pain reliever as claimed in claim 56, wherein a diode and a capacitor are provided to aid in shutting off said current regulator.

58. A transcutaneous pain reliever as claimed in claim 57, wherein energy stored in said inductive storage means is released when the current regulator is shut off.

59. A transcutaneous pain reliever as claimed in claim 58, wherein the output of the gated differentiator activates the memory flip-flop of the circuit of the next energy generator assembly.

60. A transcutaneous pain reliever as claimed in claim 59, wherein the gated differentiator of the last of said energy generator assemblies causes a DONE IN signal from the control transistor of said last energy generator to operate the trigger assembly.

61. A transcutaneous pain reliever as claimed in claim 60, wherein said inductive storage means comprises a storage winding for storing the energy and a release winding for releasing said energy to the external electrodes.

62. A transcutaneous pain reliever as claimed in claim 61, wherein a Schmitt trigger is used with the said multi-vibrator.

63. A transcutaneous pain reliever as claimed in claim 61, wherein said clocking assembly multi-vibrator includes a pair of gates.

64. A transcutaneous pain reliever as claimed in claim 63, wherein a diode is used with said clocking assembly multi-vibrator to create an asymmetric clock.

65. A transcutaneous pain reliever as claimed in claim 64, wherein a potentiometer and a fixed resistor is provided to permit the clock to be variable.

66. A transcutaneous pain reliever as claimed in claim 64, wherein a switch is provided in the clocking assembly multi-vibrator to vary the repetition rate of the output.

67. A transcutaneous pain reliever as claimed in claim 66, wherein a switch is in circuit with said anti-adapt multivibrator with associated resistors to permit the clock assembly output to be inhibited.

68. A transcutaneous pain reliever as claimed in claim 67, wherein said anti-adapt multi-vibrator comprises a pair of gates.

69. A transcutaneous pain reliever as claimed in claim 68, wherein a pair of capacitors are provided to control the frequency and include a resistor to prevent reverse bias.

70. A transcutaneous pain reliever as claimed in claim 68, wherein a single monolithic capacitor is used to control the frequency.

71. A transcutaneous pain reliever as claimed in claim 68, wherein means are provided to inhibit the anti-adapt multivibrator.

72. A transcutaneous pain reliever as claimed in claim 71, wherein said inhibit means comprises a signal from a common power source to the two gates with the signal to one gate being delayed.

73. A transcutaneous pain reliever as claimed in claim 72, wherein said delay occurs by means of a capacitor and a resistor in circuit with said delayed gate.

74. A transcutaneous pain reliever as claimed in claim 73, wherein the multi-vibrator is released when the said delayed gate rises to the condition of the other gate.

75. A transcutaneous pain reliever as claimed in claim 74, wherein release of said multi-vibrator constitutes a RESET signal.

76. A transcutaneous pain reliever as claimed in claim 75, wherein said clock assembly is in circuit with a trigger circuit, said trigger circuit comprising a flip-flop and a TRIG OUT gate.

77. A transcutaneous pain reliever as claimed in claim 76, wherein a delay circuit comprising a resistor and capacitor is associated with said trigger circuit.

78. A transcutaneous pain reliever as claimed in claim 77, wherein a completion signal from the external electrode assembly or RESET will cause the clock to operate on the trigger.

79. A transcutaneous pain reliever as claimed in claim 78, wherein a RESET signal alters the condition of the flip-flop to a condition different from the condition of the clock assembly.

80. A transcutaneous pain reliever as claimed in claim 79, wherein switch means are provided to connect the diode bridge assembly to batteries which are to be charged.

81. A transcutaneous pain reliever as claimed in claim 80, wherein switch means are provided to connect the batteries to the external electrodes.

82. A transcutaneous pain reliever as claimed in claim 81, wherein the said switch means are the same so that connections of batteries to an external electrical automatically disconnects batteries from the diode bridge assembly or connection of batteries to the diode bridge assembly automatically disconnects the batteries for the external electrodes.

83. A transcutaneous pain reliever as claimed in claim 82, wherein the output of the diode bridge assembly is absorbed by the zener diode when batteries are disconnected for the diode bridge assembly.

84. A transcutaneous pain reliever as claimed in claim 83, wherein an LED is in circuit with the diode bridge assembly.

85. A transcutaneous pain reliever as claimed in claim 84, wherein a reverse voltage protective diode is in circuit with the LED.

86. A transcutaneous pain reliever as claimed in claim 85, wherein resistor means are connected to the diode bridge assembly and wherein switch means are associated with said resistor means to permit different charging voltages to connect to the diode bridge assembly.

87. A transcutaneous pain reliever as claimed in claim 86, wherein the anti-adapt assembly and the clocking assembly are connected to the segment of the switch of the battery charger which is connected to the external electrodes.

88. A transcutaneous pain reliever as claimed in claim 87, wherein the absorption sensing mechanism of the external electrode assembly comprises an LED and a zener diode assembly.

89. A transcutaneous pain reliever as claimed in claim 88, wherein said zener assembly comprises at least one zener diode, a resistance and a transistor.

90. A transcutaneous pain reliever as claimed in claim 89, wherein said absorption sensor comprises a diode interposed between said storage means and said LED.

91. A transcutaneous pain reliever as claimed in claim 90, wherein the amount of energy passing through the absorption sensor depends on whether the voltage across the electrodes exceeds accepted values.

92. A transcutaneous pain reliever as claimed in claim 91, wherein any energy exceeding accepted values will pass through the LED to illuminate it.

93. A transcutaneous pain reliever as claimed in claim 92, wherein a diode with a resistor across it is provided in circuit with the additional inductor coil of the battery saver unit.

94. A transcutaneous pain reliever comprising a plurality of external electrode assemblies for supplying electric excitations to a patient, means for sequentially and individually pulsing a current through said external electrode assemblies, and means to prevent pulsing of current through one external electrode assembly, means responsive to the completion of a pulse from a previous external electrode assembly to pulse current through said one external electrode assembly, said pulse preventing means comprising a control transistor, said control transistor being provided for each external electrode assembly, means being provided whereby the control transistors of all but the last of said external electrode assemblies is inhibited from operating.

95. A transcutaneous pain reliever as claimed in claim 94, wherein said control transistor is inhibited because no output exists on a DONE IN line common to said plurality of control transistors.

96. A transcutaneous pain reliever as claimed in claim 95, wherein a trigger assembly is provided to pulse a signal through the external electrode assemblies.

97. A transcutaneous pain reliever as claimed in claim 96, wherein said trigger assembly is inoperative until a DONE IN signal from the control transistor is received by the trigger assembly.

98. A transcutaneous pain reliever as claimed in claim 97, wherein an energy generator assembly is interposed in circuit between said external electrode assembly and the trigger assembly and wherein said energy generator assembly activates said control transistor.

99. A transcutaneous pain reliever as claimed in claim 98, wherein a memory assembly is provided in said energy generator assembly.

100. A transcutaneous pain reliever as claimed in claim 99, wherein the energy generator assembly includes a gated differentiator.

101. A transcutaneous pain reliever as claimed in claim 100, wherein said gated differentiator supplies a pulse to said memory assembly.

102. A transcutaneous pain reliever as claimed in claim 101, wherein said energy generator assembly includes a current regulator assembly.

103. A transcutaneous pain reliever as claimed in claim 102, wherein said memory assembly comprises a flip-flop assembly including a pair of gates.

104. A transcutaneous pain reliever as claimed in claim 103, wherein the current regulator circuit is in circuit with the flip-flop assembly to control the release of energy from said inductive storage means.

105. A transcutaneous pain reliever as claimed in claim 104, wherein the condition of the output of a first gate of the flip-flop assembly is changed by a pulse from the trigger assembly.

106. A transcutaneous pain reliever as claimed in claim 105, wherein said current regulator circuit includes a darlington pair and a feedback transistor.

107. A transcutaneous pain reliever as claimed in claim 106, wherein said darlington pair having its collector load connected to the inductive storage means.

108. A transcutaneous pain reliever as claimed in claim 107, wherein said darlington pair is in circuit with the said first gate of the flip-flop.

109. A transcutaneous pain reliever as claimed in claim 108, wherein the inductor load at the collector of the darlington pair causes the feedback transistor to turn on to satisfy the current regulator.

110. A transcutaneous pain reliever as claimed in claim 109, wherein voltage on the inductor increases when said current regulator satisfies to cause an increase in voltage in a leg of said gated differentiator.

111. A trancutaneous pain reliever as claimed in claim 110, wherein said increase in voltage of said gated differentiator occurs through a capacitor and a resistor.

112. A transcutaneous pain reliever as claimed in claim 11, wherein the output of said gated differentiator resets the flip-flop of said memory circuit.

113. A transcutaneous pain reliever as claimed in claim 112, wherein resetting of said memory circuit shuts off said current regulator circuit.

114. A transcutaneous pain reliever as claimed in claim 113, wherein a diode and a capacitor are provided to aid in shutting off said current regulator.

115. A transcutaneous pain reliever as claimed in claim 114, wherein energy stored in said inductive storage means is released when the current regulator is shut off.

116. A transcutaneous pain reliever as claimed in claim 115, wherein the output of the gated differentiator activates the flip-flop of the memory circuit of the next energy generator assembly.

117. A transcutaneous pain reliever as claimed in claim 116, wherein the gated differentiator of the last of said energy generator assemblies causes a DONE IN signal from the control transistor of said last energy generator to operate the trigger assembly.

118. A transcutaneous pain reliever as claimed in claim 117, wherein said inductive storage means comprises a storage winding for storing the energy and a release winding for releasing said energy to the external electrodes.

119. A transcutaneous pain reliever comprising an external electrode assembly, means for storing energy before passage to the external electrode assembly, in absorption sensing mechanism in circuit with said storage means to indicate the amount of energy not used by the external electrodes.

120. A transcutaneous pain reliever as claimed in claim 119, wherein said absorption sensing mechanism comprises an LED and a zener diode assembly.

121. A transcutaneous pain reliever as claimed in claim 120, wherein said zener assembly comprises at least one zener diode, a resistance and a transistor.

122. A transcutaneous pain reliever as claimed in claim 121, wherein said absorption sensor comprises a diode interposed between said storage means and said LED.

123. A transcutaneous pain reliever as claimed in claim 122, wherein the amount of energy passing through the absorption sensor depends on whether the voltage across the electrodes exceeds accepted values.

* * * * *